United States Patent [19]

Butterworth et al.

[11] Patent Number: 4,553,669

[45] Date of Patent: Nov. 19, 1985

[54] STERILIZATION CONTAINER FORMED OF NONWOVEN MATERIAL

[75] Inventors: George A. M. Butterworth, Wilbraham, Mass.; William M. Evans, Mundelein; Howard J. Goldner, Highland Park, both of Ill.

[73] Assignee: American Hospital Supply Corporation, Evanston, Ill.

[21] Appl. No.: 532,462

[22] Filed: Sep. 15, 1983

[51] Int. Cl.$^4$ .................. B65D 85/50; B65D 5/68; B65D 81/24

[52] U.S. Cl. ................ 206/439; 229/23 BT; 206/484.1

[58] Field of Search ............ 206/439, 438, 484.1; 229/4.5, 23 BT, 32, 93

[56] References Cited

U.S. PATENT DOCUMENTS

| | | | |
|---|---|---|---|
| D. 218,044 | 7/1970 | Lee et al. | D30/1 |
| 2,310,818 | 2/1943 | Tompkins | 229/4.5 |
| 2,880,866 | 4/1959 | VanDyck | 229/23 BT |
| 2,990,948 | 7/1961 | Zackheim | 206/439 |
| 2,997,224 | 8/1961 | Stannard | 206/439 |
| 3,061,087 | 10/1962 | Scrivens et al. | 206/439 |
| 3,229,813 | 1/1966 | Crowe, Jr. et al. | 206/439 |
| 3,495,702 | 2/1970 | Kuster | 206/439 |
| 3,528,227 | 10/1968 | Lee et al. | 55/524 |
| 3,528,390 | 9/1970 | Lee | 156/203 |
| 3,613,639 | 10/1971 | Lee et al. | 55/524 |
| 3,727,750 | 4/1973 | Petter | 206/438 |
| 3,926,362 | 12/1975 | Beck et al. | 229/23 BT |
| 4,046,254 | 9/1977 | Kramer | 206/370 |
| 4,124,141 | 11/1978 | Armentrout et al. | 220/306 |
| 4,154,342 | 5/1979 | Wallace | 206/439 |
| 4,296,862 | 10/1981 | Armentrout et al. | 206/439 |
| 4,466,552 | 8/1984 | Butterworth et al. | 206/439 |

OTHER PUBLICATIONS 4-page Advertising Brochure for "DualWrap", by American Convertors-shows a Sterilization Wrap.
8-page Advertising Brochure for "Aesculap", by Instrumed Canada Ltd.-shows a Sterilization Container System.
8-page Advertising Brochure for "Eagle SteriSet", by Amsco-shows Sterilization Containers.
1-page Advertising Brochure for "Neomed", by Neomed/Richards-shows Sterilization Kits.
1-page Advertising Brochure for "TraySet", by DNA Medical, Inc.-shows Sterilization Trays.
5-page Advertising Brochure for "Steri Stor", by Research Surgical Systems-shows Sterilization Systems.

Primary Examiner—William T. Dixson, Jr.
Attorney, Agent, or Firm—Emrich & Dithmar

[57] ABSTRACT

A container for use in sterilization of medical items is made entirely of resin-treated, fluid repellent, semi-rigid nonwoven material. The container includes a bottom or receptacle having extending side wall or side walls and a cover having depending side wall or side walls. The material is readily permeable to gas or steam, yet is resistant to the transmission of bacteria. The container and its contents may be retrieved from a sterilizing vessel almost immediately after sterilization without special procedures or devices and without fear of being burned. Because of its low cost, the container is disposable and may be molded to a particular shape for use in shipping prosthetic devices, implants or delicate instruments in sterilized condition.

5 Claims, 4 Drawing Figures

STERILIZATION CONTAINER FORMED OF NONWOVEN MATERIAL

BACKGROUND OF THE INVENTION

The present invention relates to a container for use in the sterilization of surgical or medical items such as surgical instruments, implants and prosthetic devices. The sterilization container of the present invention is particularly suitable for, though not necessarily limited to, use in flash sterilization procedures currently used in operating suites or emergency rooms for establishing sterile conditions for these instruments and devices (collectively referred to as "medical items").

There are a number of different processes for sterilizing medical items which are recognized in the industry as effective. Examples include steam sterilization, exposure to radiation or application of a gas such as ethylene oxide. By way of example, conventional steam (i.e., autoclave) sterilization is widely used in hospital central supply areas where the item is not intended to be put to immediate use. This procedure requires exposure to steam at 250° F. for at least 15 minutes. So-called "flash" sterilization which is more commonly used in operating suites or emergency rooms, subjects the items to higher temperatures (e.g., 270° F.) for a shorter time (three minutes or more) according to well-known and professionally accepted data relating sterilization to these parameters.

Of primary consideration in sterilizing items for storage in central supply for later use is the fact that some provision must be made for maintaining sterility. This may be accomplished through special apparatus such as re-usable, metal containers with valves or filters, or by wrapping conventional open trays with commercially available sterilization wrap which may then be strip-taped for signifying that the wrapped item has been processed and, perhaps, identifying when it was processed.

These rather elaborate provisions for maintaining sterility after it is established are not of concern in flash sterilization technique because the item will normally be used immediately. Of concern in flash sterilization, however, is the convenience and speed in the use of the apparatus, the safety of the procedures employed and the acceptance of the techniques by operating personnel.

The device perhaps most commonly used for flash sterilization is an open stainless steel tray having a perforated or metal mesh bottom. Although these trays are also suitable for complete wrapping with a sterilization wrap and storage in a central supply area, they are considered useful for flash sterilization because they provide greater line-of-sight steam penetration than trays with closeable tops and quickness and completeness of steam penetration are of primary concern in flash sterilization procedures.

There are a number of disadvantages associated with such conventional trays currently used to flash sterilize medical items. One of the more common disadvantages with the apparatus is that of weight. Metal trays, whether stainless steel or aluminum, are heavy. The added weight of instruments makes these trays even more difficult in handling and manuevering.

Another disadvantage of metal trays is that their temperature remains high following sterilization; and special precautionary procedures are sometimes required to handle them. For example, clamps or cushioned heat pads are sometimes used in handling metal trays immediately following steam sterilization. Further, there is a tendency for condensate to form on metal trays used in steam sterilization procedures. Special precautions to prevent accumulation of excess condensate, such as lining the bottom of the tray with towels are sometimes taken with conventional metal trays.

Another disadvantage of metal trays having perforated or mesh bottoms is that even stainless steel is subject to corrosive attack or oxidation in the extremely hostile environment of repeated exposure to steam.

SUMMARY OF THE PRESENT INVENTION

The present invention provides a sterilization container for holding medical or surgical items which is particularly suited for use in flash sterilization processes, although it is not limited to such use. The present device overcomes many of the problems associated with conventional metal trays.

The container of the present invention includes an open receptacle and a cover which sealingly engages and closes the receptacle about its full periphery. Both the receptacle and cover are made entirely of resin-treated non-woven material which is fluid repellant and provides a bacterial barrier, yet is readily gas permeable to provide a complete spherical line-of-sight permeability for steam. The nonwoven material is formed into the desired shapes of the respective receptacle and cover. The container is semi-rigid and will retain its shape under normal use conditions. As used herein, "semi-rigid" means that the material, in its final condition, will not lose its shape under ordinary use conditions. In other words, like a folded carton cardboard container, the container of resin-treated nonwoven material can be stacked, dropped, carried with contents, etc. without buckling, creasing or permanent deformation.

Preferably, a discontinuous surface seal (i.e., having two separate, non-planar surfaces) or other non-planar surface seal (such as is formed by a curved seal rim or bead) is formed between the receptacle and the cover. This may be formed by having the upper edges of the side walls lie in a common plane and contacting the under surface of the top of the cover. The second seal surface is formed by the contact between the outer surface of the side wall of the receptacle and the inner surface of the depending side wall of the cover. Such a discontinuous surface seal is effective as a barrier to air-borne contaminants as well as a bacteria barrier and may permit post-procedure storage for a period of time without compromising sterility.

The present container is inexpensive enough that it may be discarded after use. The nonwoven material is more resistant to tearing and puncture than commercially available sterilization wrap.

The present invention thus provides a simple, economical structure which overcomes some major problems existing in current apparatus used in flash sterilization in addition to the high cost of existing equipment. Because it is non-metalic, the present container can be handled immediately after sterilization and even acts to isolate the hands from the sterilized item which may be metal and still hot.

Another advantage of the present invention over existing commercial apparatus is the light weight of the container. Despite the light weight, however, the inventive container is capable of carrying relatively heavy instruments without deforming or collapsing.

By employing nonwoven material for both the receptacle and the cover, there is a straight line-of-sight path for steam through the container from every incident angle since the nonwoven material is permeable to steam. This facilitates sterilization and may ultimately reduce the time required to achieve reliable sterilization. The use of nonwoven material has the further advantage that the container and contents can be handled immediately after sterilization without special tools or procedures and without fear of a burn, yet it retains its semi-rigid structural integrity. Another advantage of the present invention is that there is no likelihood of corrosion that might otherwise occur in the use of metal sterilization trays when the metal of the tray is different from the metal of the instrument or article being sterilized. Obviously, the nonwoven material itself is not subject to corrosion (as in the case of metal sterilization trays) despite the length of time or the degree of steam temperature used.

The light weight, bacterial barrier properties, and low heat capacity of the nonwoven sterilization container of the present invention provides opportunities for new sterile technique management methods. For example, by making the receptacle and lid in the form of elongated tubes with cylindrical side walls, presentation of the sterilized item is facilitated by having the length of the receptacle less than the length of the item contained in it; but the combined length of receptacle and cover are sufficient to enclose the item when they are assembled. When the cover is removed after sterilization, a part of the item protrudes beyond the receptacle to permit the physician or circulating nurse to grasp it directly while it is being held in the receptacle.

The nonwoven material used to form both the receptacle and the cover are preferably treated to be fluid repellant; and these desirable characteristics are retained after sterilization. One advantage inherent in the use of nonwoven materials is that they maintain no static electrical charge, and this is an important safety feature particularly in surgical suite usage.

To summarize the advantages of the container of the present invention over prior open metal trays, it is lighter, more maneuverable, and is capable of being removed from sterilization apparatus without heat pads or special handling procedures. It also does not require a large initial expenditure to implement the system. The instant container may be provided in a wide variety of sizes or shapes, and may be adapted for use with auxiliary trays or special inserts for sharp or delicate instruments.

With respect to so-called reusable systems, the light weight and reduced initial cost of the present invention are even more pronounced. The present container also affords advantages of simplicity and reduced tendency of human error. Since the nonwoven container material possesses properties that make it an excellent bacterial barrier, it enables a much simpler procedure for assembly and obviates the need for special valves or filters. Of particular importance is the fact that if properly handled, the present container prevents possible contamination in opening the container and presentation of its contents.

Other features and advantages of the present invention will be apparent to persons skilled in the art from the following detailed description of a preferred embodiment accompanied by the attached drawing, wherein like reference numerals will refer to identical parts in the various views.

DETAILED DESCRIPTION OF THE DISCLOSED EMBODIMENT

As used herein, the term "nonwoven" is used in the sense that the term is understood by persons skilled in the hospital supply industry. In particular, the term refers to a nonwoven fabric or web of continuous filaments—e.g., polyester—which is permeable to air or steam but prevents the transmission of bacteria. In contrast to a woven fabric which has a comparatively large pore size, a nonwoven has a larger number of much smaller pores with no line-of-sight porosity. It is this structure which permits steam penetration but prevents entry of bacteria. The term may also include standard long textile fiber nonwovens or paper-derived nonwovens capable of providing a bacterial barrier.

The nonwoven web or fabric is treated with a resin (e.g., a water soluble epoxy, acrylic, phenolic or polyester resin) which remains partially cured until the resin-treated material is placed in a mold formed to the desired shape and heat-treated. The application of heat completes the cure of the resin, and the material takes on the shape of the mold and remains semi-rigid. The article retains its semi-rigid structure even after steam sterilization, yet remains porous and readily permeable to steam.

One suitable commercially available material for obtaining a semi-rigid posture after treatment is sold under the designation "800621" by The Technical Fabrics Division of Albany International of Auburn, Me. Other nonwoven materials having these structural characteristics together with the ability to provide a bacterial barrier may equally well be employed.

Figure 1:
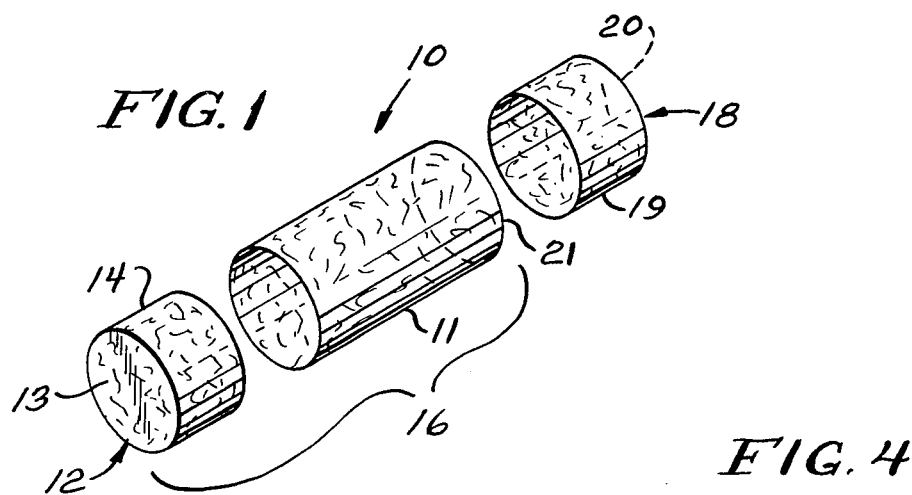
FIG. 1 is a perspective, exploded view of a sterilization container in tubular form incorporating the present invention.

Referring first to the embodiment of FIG. 1, reference numeral 10 generally designates a tubular center portion forming a continuous cylindrical side wall 11 of the assembled container. The end cap 12 has a flat end wall 13 and an integral cylindrical side wall 14 which is sized to fit over and preferably continuously engage the edge and the end wall 11 of the tubular center portion 10 of the container to form a discontinuous surface seal as will be described.

When the tubular portion 10 is thus assembled to the first end cap 12, a receptacle designated by the bracket 16 is thus formed for receiving items to be sterilized. If economy of shipment and storage are not particularly important, the end cap may be assembled and even bonded to the tubular center section, making a one-piece receptacle.

After the items are inserted into the receptacle 16, a second end cap generally designated 18 and including a cylindrical side wall 19 and a flat end wall 20 are used to cover the open end of the receptacle 16. Again, the cylindrical side wall 19 is sized to contact continuously the outer surface of the side wall 11 in snug, frictional engagement. Alternately, where a discontinuous surface or double seal is not necessary, as in flash sterilization procedures, the axial length of the removable end cap 18 may be extended so that even though a substantial portion of the end cap 18 does engage the outer surface of the side wall 11, the end cap 18 may nevertheless extend well beyond the edge 21 of that side wall. Thus, items placed within the receptacle 16 may extend beyond the planar edge 21 of the side wall 11 to facilitate grasping by a circulating nurse or operating room personnel during presentation and without the need for special instruments.

The entire container shown in FIG. 1, including the tubular center portion 10 and the end caps 12, 18 is formed of nonwoven material.

Figure 2:
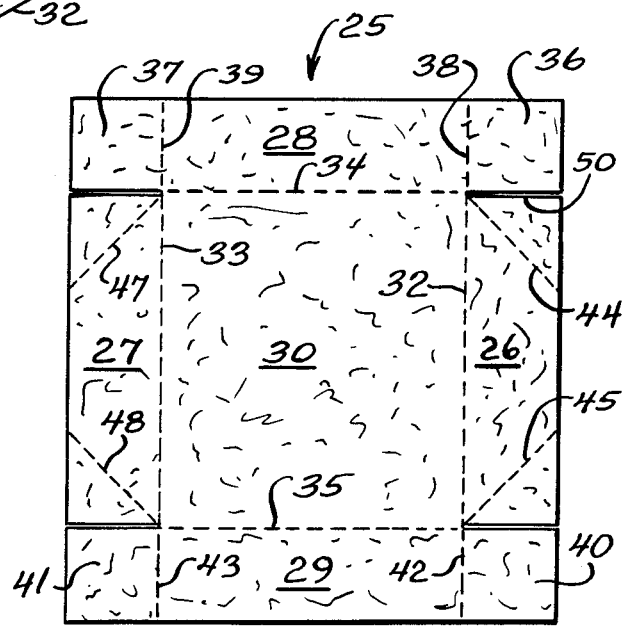
FIG. 2 is a plan view of the blank from which a receptacle or cover of a second embodiment of a sterilization container may be formed.

Turning now to FIG. 2, a second embodiment in the form of a "knock down" or folded carton will be described. The tray and cover of such a carton, preferably being rectangular in form, may be formed similarly, so only one need be described in detail for a person skilled in the art to understand the other completely. The cover, course, would be slightly larger than the tray, again, with the purpose and effect of establishing a discontinuous surface seal including continuous contact between the inner surface of the depending side walls of the cover and the outer surface of the upstanding side walls of the tray, as will be more fully understood from the following description.

Turning first to FIG. 2, the tray may be formed from a die-cut blank generally designated 25. The blank 25 is formed entirely of nonwoven materials and is cut to form a first side wall 26, a second, opposing side wall 27, a third side wall 28, a fourth side wall 29 and a bottom 30. The side walls 26, 27 are partially formed by fold lines 32, 33 respectively. Similarly, side walls 28, 29 are partially defined by fold lines 34, 35. Further, side wall 28 is provided with end tabs 36, 37 which, in turn, are partially defined by fold lines 38, 39. Similarly, side wall 29 is provided with end tabs 40, 41 which are partially defined respectively by fold lines 42, 43.

Inclined fold lines 44, 45 are also formed in the side wall 26, and similar inclined fold lines 47, 48 are formed in the side wall 27.

In forming the tray 25, the side walls 28, 29 are first placed upright relative to the bottom 30; and end tabs 36, 37 and 40, 41 are folded inwardly (that is, at right angles relative to their associated side walls).

The opposing side walls 26, 27 are then folded upwardly so that the end tabs of the first pair of side walls are adjacent the inner surfaces of the side walls 26, 27. Next, the outboard vertical edges of the side walls 26, 27 are secured to the corners of the respective adjacent edges of the end walls 28, 29. For example, the edge 50 of the side wall 26 is attached to the outer surface of the end wall 28 adjacent the fold line 38 of that end wall. The bond may be accomplished along the corner seams of the end walls 28, 29 by any suitable means such as dielectric sealing, ultrasonic heat or suitable adhesive. The end tabs 36, 37 however, should be free to fold so that the tray (or the cover) can be collapsed for economy of space in shipment or storage.

Figure 3:
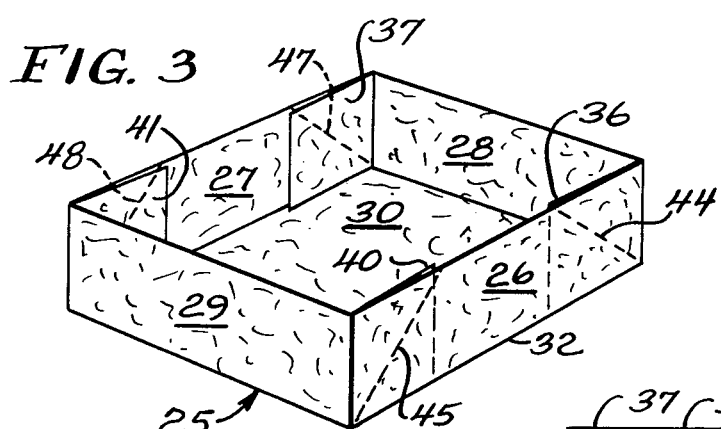
FIG. 3 is a perspective view of the receptacle or cover of FIG. 2 in assembled form.

Referring to FIG. 3, the tray 25 is shown in assembled format wherein the tabs 36, 37 of the side wall 28 are folded outwardly against the inner surfaces of the adjacent side walls 26, 27. Similarly, the end tabs 40, 41 of the side wall 29 are folded outwardly (that is, at right angles to the vertical plane of the end wall 29) to contact the inner surfaces of the adjacent end walls 26, 27 respectively.

In order to fold the tray of FIG. 3 for shipment or storage, the tabs 36, 37 are rotated 90° against the inner surface of the end wall 28 (tabs 40, 41 are similarly rotated until they contact the end wall 29); and the side walls 26, 27 are then collapsed by folding along the inclined fold lines 44, 45 and 47, 48 respectively so that the end walls 28, 29 then fold down on top of the side walls 26, 27 to form a generally flat element.

Figure 4:
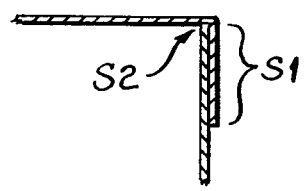
FIG. 4 is a fragmentary vertical cross-section showing two non-planar sealing surfaces of an assembled cover and receptacle.

The upper edges of the side walls 26-29 all terminate in a common plane so that when a correspondingly shaped, but slightly larger cover is placed on the receptacle 25, two separate seals are formed. The first seal is formed through the snug continuous contact between the outer surfaces of the side walls of the receptacle 25 and the inner surfaces of the depending side walls of the cover. This seal alone precludes air-borne contaminants from entering the sealed container. The second seal, which is preferably continuous throughout the periphery of the container, is formed between the upper edges of the side wall and the lower surface of the top panel of the cover. Thus, in both embodiments there is provided a discontinuous (i.e., non-planar) path for sealing against the entry of bacteria. Specifically, the path includes a first elongated section over which the outer surface of the side wall of the receptacle is in contact with the inner surface of the depending side wall of the cover (as indicated by the section designated S1 in FIG. 4), and a second section in which the upper edge of the side wall (embodiment of FIG. 1) or side walls (embodiment of FIG. 3) lies in a plane and is in contact with the lower planar surface of the cover, as represented by the area designated S2 in FIG. 4.

The present invention may be used in all the various current processes for sterilizing medical items. In subjecting the container and its contents to steam sterilization, it will be appreciated that there is line-of-sight permeability of the steam from all incident angles, unlike the limited access in the case of solid stainless steel walls of some prior sterilization trays or the "reusable" containers of the prior art described above. This is considered an important advantage in insuring complete and rapid sterilization of articles of all sizes and shapes.

Because of the low heat capacity and low mass of the nonwoven material, there is little or no condensation of the steam on the surface of the container, thereby precluding bacterial "strike through" via a fluid path. The use of nonwoven fabric enables a person to remove the container almost immediately after sterilization and without fear of burn or discomfort. The container acts as a insulator against the heat of the sterilized item, if it is metal. Handling of the container and contents is made easier due to the lighter weight of the nonwoven material.

The light weight of the nonwoven material, in contrast to prior stainless steel trays, affords greater flexibility and less likelihood of dropping the contents. The lid and tray maintain their semi-rigid nature due to the resin content of the nonwoven material and the structural rigidity designed into the members, as described above.

The nonwoven container material preferably is treated with an agent to provide fluid repellency which characteristic is maintained even after sterilization. One suitable agent for making the nonwoven fluid repellent is available under the trademark "SCOTCHBAN" from 3M Co. of Minneapolis, Minn. The material may also be treated with a fixed antimicrobial agent to increase sterile storage time.

Another advantage of the present invention is that it may be molded to any desired shape while maintaining the discontinuous seal path mentioned above. For example, it may be in either of the shapes illustrated in the drawing, or it may be formed to specifically fit a prosthetic device, delicate instrument or a sharp instrument. The container provides not only protection for the contents but prevents damage by the contents as in the case of a sharp instrument. The container can be used as a separate insert container for larger sterilization containers, even the reusable containers of the prior art. It may serve as a sterilization container for the shipment of prostheses or instruments by a manufacturer so that original sterility can be established by the manufacturer and maintained during shipment.

Having thus disclosed alternate embodiments of the invention, persons skilled in the art will be able to modify certain of the structure which has been illustrated and to substitute equivalent materials for those illustrated, while continuing to practice the principle of the present invention. It is therefore intended that all such modifications and substitutions be covered as they are embraced within the spirit and scope of the appended claims.

We claim:

1. A sterilization container capable of withstanding steam sterilizaion without substantial change in physical properties comprising: a receptacle of fluid-repellant, semi-rigid nonwoven material and including a bottom and upstanding side wall means integral with said bottom; and a cover of fluid-repllellant, semi-rigid nonwoven material and including a top, and depending side wall means conforming in shape with said side wall means of said receptacle and sized to engage frictionally and continuously the outer surface thereof to provide a bacterial seal when said receptacle and cover are assembled; said cover and container characterized in that they retain their respective semi-rigid properties after sterilization and are capable of supporting and maintaining the sterility of the contents thereof.

2. The article of claim 1 wherein there is substantial overlap and continuous engagement between the outer surface of the side wall means of the receptacle and the inner surface of the depending side wall means of the cover.

3. The article of claim 2 wherein the side wall means of said receptacle defines an upper edge portion extending in a common plane and is adapted to engage continuously the under surface of the top of said cover when said cover is assembled to said receptacle thereby to define a discontinuous surface seal path between said cover and said receptacle.

4. The article of claim 3 wherein said side wall means of said receptacle and said cover are generally circular in cross-section.

5. The article of claim 3 wherein said side wall means of said cover and said receptacle are generally rectangular in cross-section.

* * * * *